United States Patent [19]

Schneider et al.

[11] Patent Number: 4,813,779
[45] Date of Patent: Mar. 21, 1989

[54] PERIMETER

[76] Inventors: Richard T. Schneider, 17 Alachua Highlands, Alachua, Fla. 32615; Richard H. Keates, 264 N. Drexel Ave., Columbus, Ohio 43209

[21] Appl. No.: 6,972
[22] Filed: Jan. 23, 1987
[51] Int. Cl.$^4$ ............................................. A61B 3/02
[52] U.S. Cl. ................................... 351/226; 351/237; 351/246
[58] Field of Search ............... 350/96.24, 96.25, 96.26; 351/226, 237, 239, 243, 246

[56] References Cited

U.S. PATENT DOCUMENTS

| | | | |
|---|---|---|---|
| 4,045,130 | 8/1977 | Krahn | 351/226 |
| 4,146,311 | 3/1979 | Murr | 351/226 |
| 4,483,585 | 11/1984 | Takami | 350/96.24 |

Primary Examiner—John K. Corbin
Assistant Examiner—Jay Ryan
Attorney, Agent, or Firm—Bert J. Lewen

[57] ABSTRACT

A perimeter having an image projection system which projects an undistorted line target across the full range of a patient's field of vision is disclosed. The image projection system includes a projector, a bundle of optical fiber elements, and lenses associated with the optical fiber elements adapted to focus the target onto the observation hemisphere of the perimeter. The perimeter may also be provided with a fixation monitor system which monitors the patient's gaze and which will interrupt projection of the target when fixation is lost. The fixation monitor includes at least one sensor for detecting the intensity of infrared light reflected off the patient's eye, and a comparator adapted to compare the output signals from each sensor during the examination with base signals obtained at fixation. Any signal variation will indicate that fixation has been lost and projection of the target will be interrupted. Projection will resume once fixation has been reestablished.

12 Claims, 3 Drawing Sheets

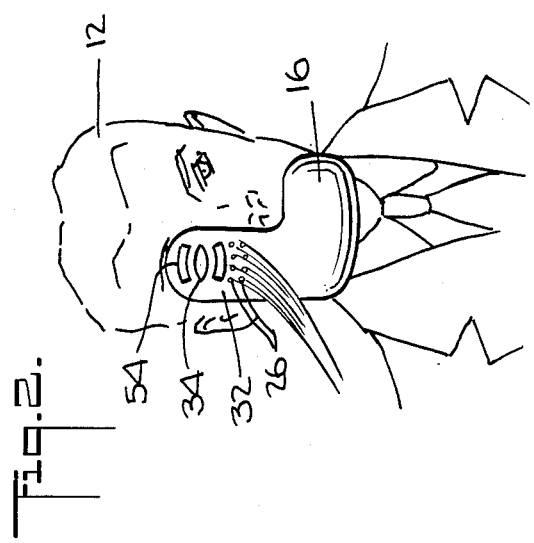
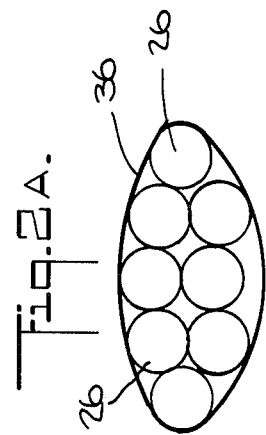
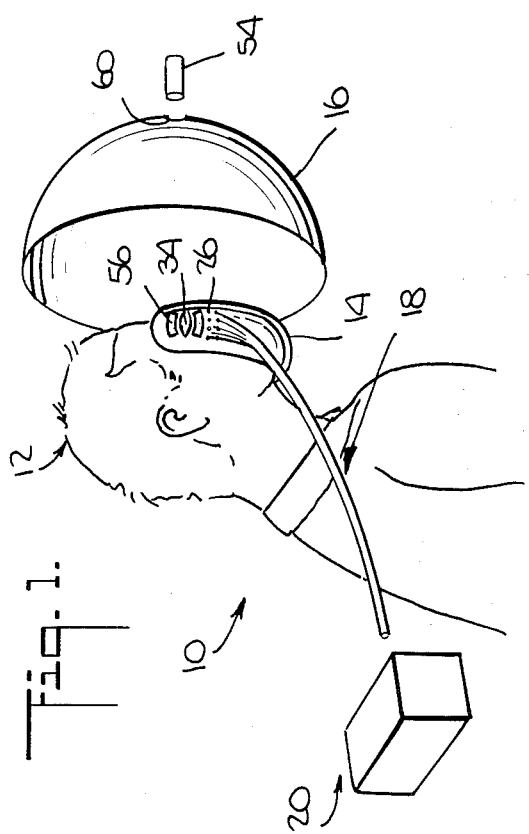
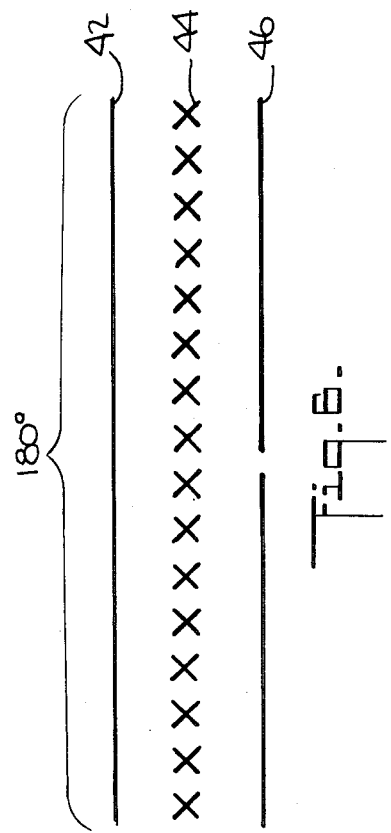

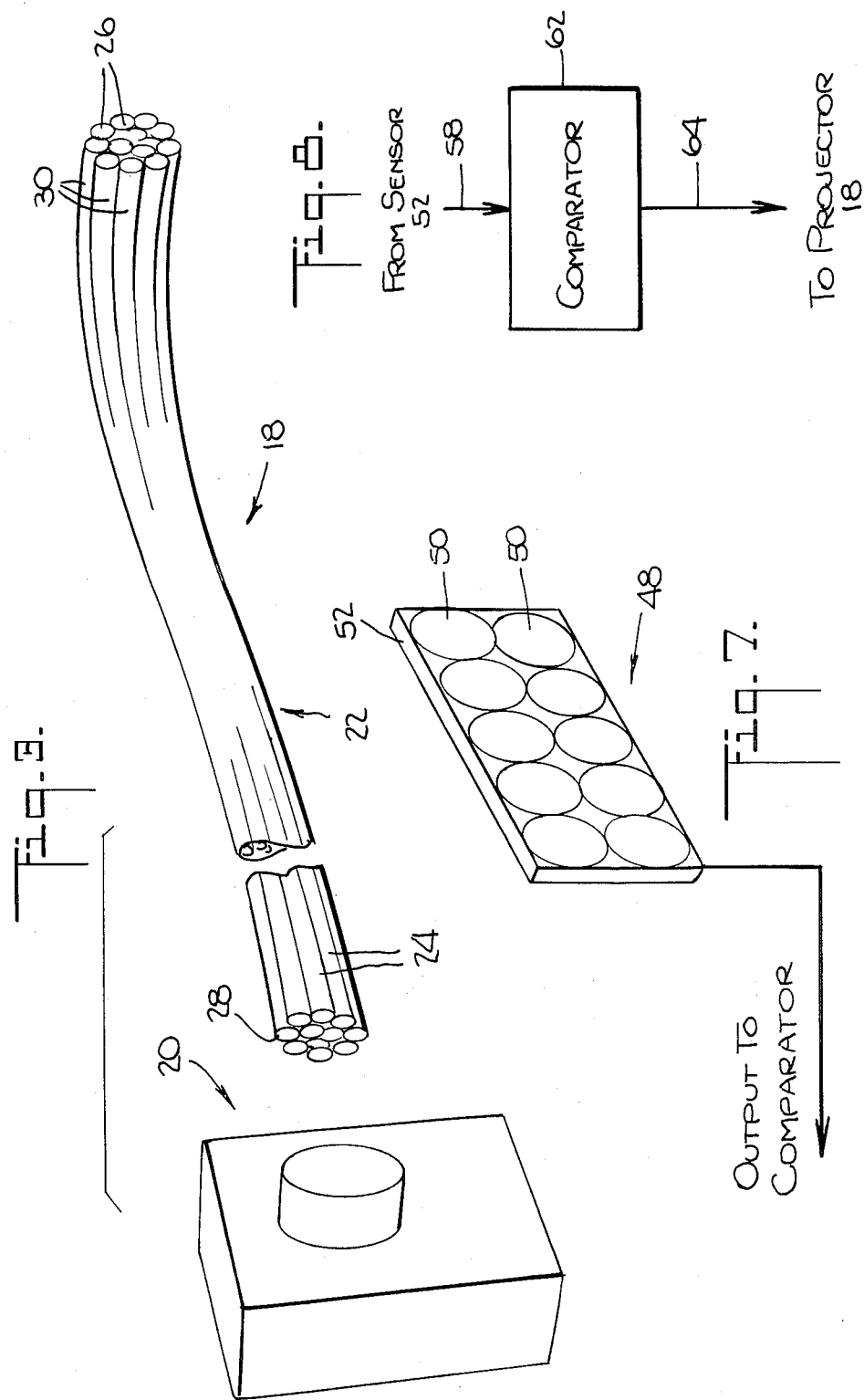

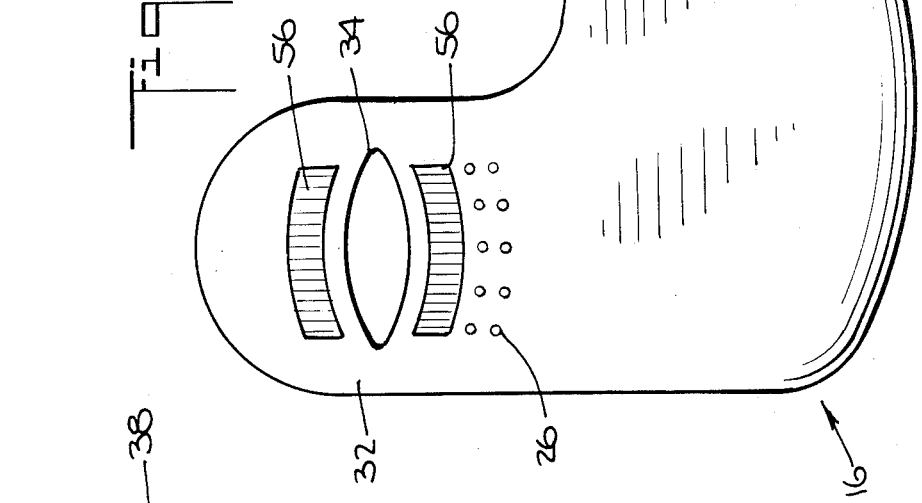
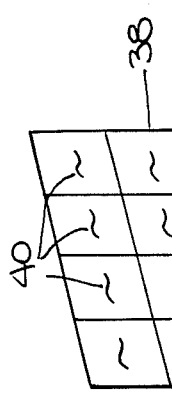
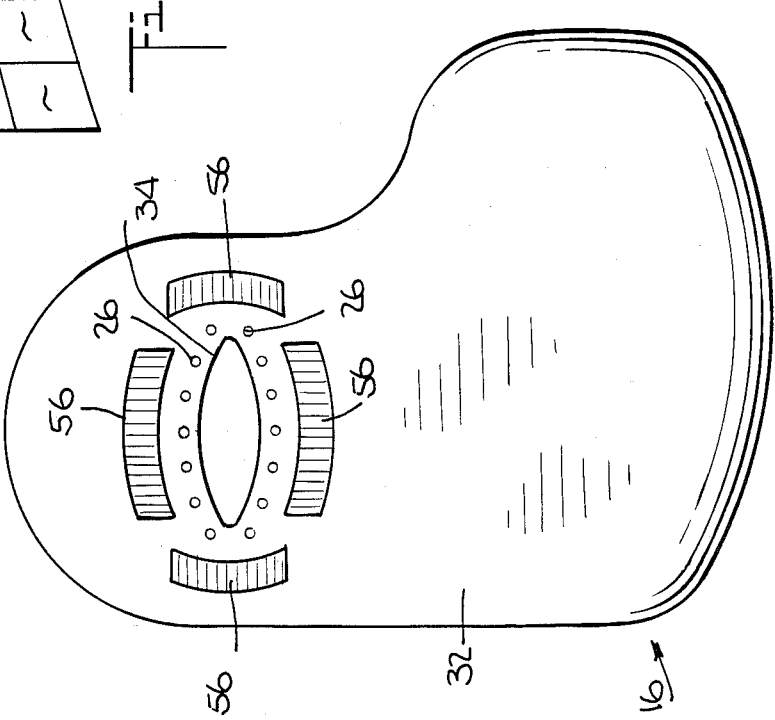

PERIMETER

BACKGROUND OF THE INVENTION

This invention relates to perimeters for visual field testing, and more particularly pertains to an improved image projection system and an improved fixation monitoring system for such devices.

Many modern perimeters for testing the visual field, whether manual or automatic, consist of a hemispheric bowl or observation hemisphere which is evenly illuminated. The patient looks at a central fixation point while spots of light or targets of various sizes and intensities are projected at various places within the observation hemisphere and the patient indicates whether or not the target is visible. The field of view is then mapped out point-by-point on a chart, sometimes with the aid of a computer.

Visual field testing involves not only the determination of the extreme outside boundary of the visual field but the identification of any regions of relative blindness within that field. Testing usually includes static threshold perimetry and kinetic or dynamic perimetry. In static threshold perimetry, a location is chosen and the target is presented at that location without moving it. The target is increased in intensity (or size) until it becomes visible, determining the visual threshold at that location. This process is then repeated at other points. In kinetic or dynamic perimetry, a selected target is moved from an area where it is not seen toward an area where it is seen and the location where the target becomes visible is recorded. This process is repeated from all directions toward the center (fixation) until an isopter or line can be drawn connecting the points where the target first became visible. Several isopters can be drawn by repeating the process with several targets of differing intensity or size. Since it is normal for a test stimulus to be seen everywhere within the region bounded by an isopter, the region can be scanned to locate areas where the target is not seen, i.e., the physiologic blind spot and areas of relative blindness. To conduct such testing utilizing spot stimuli is laborious, suffers from inaccuracies and is time consuming.

Obviously the validity of these tests depends on the patient correctly reporting what he sees or does not see. During the examination there is an urge for the patient to look at the target in order to see it better. Since a data point must be rejected if fixation was not established at the instant the data point was taken, the examiner has to constantly check that the patient's eye remains fixed on the central fixation point. Obviously, it is no good for the examiner to check fixation after the patient responds. The patient may have looked at the target and responded, and regained fixation before the examiner checks. Typically fixation is checked by the examiner observing the pupil of the patient's eye through a telescope which is located behind the fixation point. Recently electronic motion detectors have been used to check eye fixation automatically.

Vision field testing is a painstaking procedure for the patient as well as the examiner and the cooperation of the patient diminishes after a while and is sometimes lost altogether.

Thus, it is desirable to provide a perimeter which projects an effective target across the assumed viewing range of the patient and which prevents recording of invalid data.

OBJECTS AND SUMMARY OF THE INVENTION

Among the several objects of the invention may be noted the provision of a novel perimeter for testing the visual field which projects an undistorted line target across the assumed range of the patient's field of view, and a novel perimeter in which the recording of invalid data points is prevented.

Other objects and features of the invention will be in part apparent and in part pointed out hereinafter.

In accordance with the present invention, the perimeter includes an observation hemisphere, and a chin rest adapted to support the patient's head and which is adjustable to allow for proper positioning of the patient's head with respect to a central fixation point in the observation hemisphere. An image projection system projects an undistorted line target across the assumed range of the patient's peripheral vision field. The image projection system includes a projector containing a slide or film transparency of the target, a bundle of optical fiber elements, and lenses associated with the optical fiber elements to focus the target image on the observation hemisphere. The slide or film transparency may consist of several identical image cells, the image from each cell falling on the light receiving end of one of the optical fiber elements.

The lenses are positioned immediately adjacent the patient's eye, above or below it, or may be positioned surrounding the eye. The lenses are arranged so that the projected target covers a range greater than the assumed field of view of the patient. A projection range of 180 degrees is preferred.

The line target which can be moved systematically throughout the vision field can have gaps, numbers, letters, or symbols placed in strategic locations which the patient would have to detect. If the patient has a vision deficiency, he will indicate gaps in a target where none exist.

The perimeter may also be provided with a fixation monitor which continuously monitors the patient's gaze and which interrupts projection of the test pattern during periods of nonfixation.

The fixation monitor includes an infrared light source adapted to direct infrared light onto the patient's eye, and detectors to receive the infrared light reflected off the eye. Base signals representative of the intensity of the light reflected onto the detectors at fixation is obtained at the beginning of the examination once the examiner has determined fixation using traditional methods. These base signals are stored in a comparator which may be a computer. As the examination proceeds, the output signals from the detectors are compared with the base signals stored in the comparator. Any variation in the signals will indicate that the patient's eye has moved and that fixation has been lost. Projection of the test pattern will be interrupted, to be resumed automatically once fixation is reestablished as confirmed by the detected signals matching the base signals.

The invention accordingly comprises the constructions and methods hereinafter described, the scope of the invention being indicated in the claims.

DESCRIPTION OF THE DRAWINGS

In the accompanying drawings, in which several embodiments of the invention are illustrated, FIG. 1 is a front perspective view of a perimeter embodying the present inventions;

FIG. 2 is an enlarged fragmentary perspective view illustrating one aspect of the present invention, and FIG. 2a illustrates a possible lens configuration of the invention;

FIG. 3 is a schematic view of the image projection system of the present invention;

FIGS. 4a and 4b are similar to FIG. 2 and illustrate alternative embodiments of the present invention;

FIG. 5 is an enlarged perspective view of a slide transparency utilized in the present invention;

FIG. 6 illustrates possible targets that can be projected;

FIG. 7 is an enlarged schematic view of the fixation monitoring system of the present invention; and FIG. 8 is a flowchart for detecting loss of fixation.

Corresponding reference characters indicate corresponding parts throughout the several views of the drawings.

DETAILED DESCRIPTION OF THE INVENTION

A perimeter incorporating the subject inventions is identified generally by the reference numeral 10 in FIG. 1. A patient 12 is shown with his head supported in a chin rest 14 looking into a hemispherical bowl or observation hemisphere 16 onto which a test pattern is projected.

The perimeter 10 includes an image projection system identified generally by reference numeral 18 which is adapted to project an undistorted line target across the patient's assumed peripheral field of view along selected horizontal, vertical, or inclined axes, instead of the spot or point target of traditional perimeters. With reference to FIG. 3, the image projection system 18 is shown schematically as including a projector 20, a bundle of flexible optical fiber elements or sub-bundles 24, which in turn comprise each a large number of optical fibers, and lenses 26 associated with the optical fiber elements 24.

The projector 20 can be a conventional slide or film projector or a projection television depending on whether static or dynamic perimetry is to be performed as will be discussed below. The flexible bundle 22 permits the projector 20 to be located out of the way of the patient and in a location readily accessable to the examiner so that the slide or film may be changed easily. The image on the slide or film transparency in the projector 20 is focused on the light receiving ends 28 of the optical fiber sub-bundles 24 and is projected onto the observation hemisphere 16 by the lenses 26 positioned at the light emitting ends 30 of the optical fiber sub-bundles 24. It is preferred that each optical fiber sub-bundle 24 have a separate lens 26 associated therewith. The lenses 26 have a short focal length and may be typically 4 mm in diameter. Ten or more optical fiber sub-bundles each containing typically 1000 optical fibers may be included in the bundle 22.

It is desirable that the projected target extend across the assumed peripheral field of vision at selected angles, i.e., horizontally, vertically, or inclined, and with little or no distortion. It has been found that the boundaries of the field of vision measured from the point of fixation (the object at which the eye is directed) are approximately: 60 degrees superiorly (above); 75 degrees inferiorly (below); 100 degrees temporally (to the right for the right eye, to the left for the left eye); and 60 degrees nasally (to the left for the right eye, to the right for the left eye). Thus the projected target should extend a full 180 degrees across the observation hemisphere to insure the patient's peripheral range is included in the test.

In conventional perimeters, the projector is located behind the patient, e.g., over the left or right shoulder, which configuration limits the range over which the target can be projected.

To insure full and distortion free projection, the lenses should be positioned in close proximity to the patient's eye. With reference to FIGS. 2 and 4a and b, the chin rest 16 has an integral upwardly extending portion 32 covering the cheek of the patient which is provided with an aperture 34 through which the patient views the observation hemisphere. The positioning of the chin rest relative to the aperture can be adjusted to accommodate different patients and the the specific arrangement of parts to do so would be obvious to one skilled in the art and will not be described in detail herein.

The lenses 26 shown in FIGS. 2 and 2a cover the surface of a hemisphere 36 mounted to the chin rest in any suitable conventional manner beneath the aperture 34, thus making it possible that the observation hemisphere is fully and distortion free filled with the projected image. The number of lenses provided along with their location with respect to the aperture may vary. For example, as shown in FIG. 4a, the lenses 26 may be equally spaced around the circumference of the aperture 34. It will be appreciated that the flexible optical fiber elements permit wide freedom of design for the lens configuration and their placement and other configurations are possible without detracting from the spirit and scope of the invention provided that the projected target is in focus and free of distortion. Furthermore, the lenses 26 can be supported on appropriate mounting means independent of the chin rest.

The image projected onto the light receiving ends of the optical fiber elements may be reduced in size as compared to the image on the slide. As shown in FIG. 5, a slide transparency 38 may contain several image cells 40, in which case the light receiving ends 28 of the optical fiber elements 24 are arranged so that the image created by each cell falls onto its associated element end 28 and the lenses 26 are arranged so that the projected test pattern is coherent and distortion free. Preferably, in such embodiments the image in each cell 40 is modified prior to placement on the slide 38 using conventional computer aided design technology to cancel distortions due to lens abberations. This arrangement permits an undistorted line target to be projected over a range of 180 degrees on the observation hemisphere, even when single element short focal length projection lenses are used.

The systematic projection of a series of line targets over the patient's full peripheral field allows for more creative approaches to static and dynamic perimetry. Examples of possible targets are shown in FIG. 6. A line target could be a continuous unbroken line 42, or consist of numbers, letters, or symbols 44 or have a gap 46 at strategic locations that the patient would have to detect or the projected target may be outlines of the expected field of view filled with annular rings of the same shape. This procedure is quite different from and more effective than the patient having to identify spot stimuli. Furthermore, it aids in identifying vision deficiencies such as blind spots. Where such deficiencies exist the patient will see a gap in the target or an island in the set of annular rings. If the patient should for some reason try to suppress the fact that he sees such an island, artificial islands can be periodically projected, unknown to him. Therefore more convincing measurements can be made in this manner than with point stimuli. Dynamic perimetry testing may involve the projection of a series of letters or numbers which the patient would read. As the frames advance, the target set moves closer and closer to the known blind spot and eventually would be on it, at which time the patient would report that nothing is seen. This same method can be used to locate and size islands of insensitivity or denegration on the retina much more quickly and with much greater accuracy then with spot stimuli.

As noted hereinabove, it is important that the patient maintain fixation during testing. Accordingly, a novel gaze monitoring system is provided to assure that no data will be recorded during periods of nonfixation. Basically, the intensity of infrared light reflected from the patient's eye during the examination is compared with that measured at fixation. Any variation will cause an interruption in the projection of the target.

Referring now to the drawings, a fixation monitoring system is identified generally by the reference numeral 48 is shown schematically in FIG. 7. The system 48 includes a plurality of short focal length, small diameter lenses 50. Typically, each lens 50 has a diameter of 3 mm and a focal length of 6 mm. Infrared sensitive detectors or sensors 52 are positioned in the focal plane of the lenses 50. Such sensors may be model IS32A manufactured by Micron Technology, Inc. Infrared light from source 54 (FIG. 1) is directed onto the patient's eye. The light should have a wavelength of between 800 mm and 1000 mm since this band is invisible to the human eye and will not distract the patient.

Preferably, the lenses and sensors are positioned in close proximity to the patient's eye to receive the infrared light reflected therefrom. Two possible configurations are shown in FIGS. 4a and 4b. A lens and sensor arrangement 56 can be mounted to the chin rest extension above and below the aperture 34 as in FIG. 4b or above, below and on either side of the aperture 34 as shown in FIG. 4a. The particular configuration selected will depend upon the lighting situation, but the configuration of FIG. 4b has been found to be adequate in most cases.

The sensors 52 as shown in the flowchart in FIG. 8, will generate output signals 58 representing the image of the iris in infrared light focused by the lenses onto the sensors. At the beginning of the examination the examiner will check fixation using conventional techniques, i.e., sighting through the central fixation point 60 with a telescope (not shown) to establish fixation. The output signal from each sensor namely the image of the iris is stored in digital form in the microprocessor memory as a base signal in suitable comparator means 62. Continuously during the course of the examination, the output signals from each sensor are monitored and compared to the base signal for that sensor established at fixation. Any variation represents a movement of the iris indicating that fixation has been lost. A signal 64 will then be sent to interrupt the projection of the target image so that the patient will no longer see a target and no data can be taken. Once the output signals from the detectors match the base signal thus indicating that the patient has regained fixation, the target image is again projected, the patient sees again the target and the examination can continue.

While both the novel projection system and novel fixation monitoring system have been discussed as components of the same perimeter, it will be appreciated that either system can be incorporated into a perimeter without the other, although the effectiveness of the perimeter is greatly improved when both systems are present.

Some advantages of the present invention evident from the foregoing description include a perimeter in which a line target is projected across the patient's assumed peripheral range of view. A further advantage is the ability to interrupt projection of the target during periods in which the patient has lost fixation. The automatic cessation of projection will train the patient very effectively to maintain fixation, more than sounding buzzers would do.

In view of the above, it will be seen that the several objects of the present invention are achieved and other advantageous results attained.

As various changes can be made in the above constructions and methods without departing from the scope of the invention, it is intended that all matter contained in the above description or shown in the accompanying drawings shall be interpreted as illustrative and not in a limiting sense.

What is claimed is:

1. A perimeter comprising:
   (a) an observation hemisphere having a central fixation point;
   (b) means for supporting a patient's head and which is adjustable for proper positioning of the patient's head with respect to the central fixation point; and
   (c) image projection means constructed and arranged to project a distortion free target onto said observation hemisphere, said target extending across the full assumed range of the patient's peripheral vision field, said image projection means including:
      (i) a projector adapted to generate an image from a transparency;
      (ii) a plurality of flexible optical fiber elements, each having a light receiving end and a light emitting end, the light receiving end of each optical fiber element arranged to receive the image from said projector; and
      (iii) a plurality of lenses each being positioned in close proximity to the patient's head support means at the light emitting ends of said optical fiber elements and being collectively adapted to focus said image onto said observation hemisphere.

2. The perimeter as claimed in claim 1 wherein said target extends 180 degrees across the patient's field of vision.

3. The perimeter as claimed in claim 1 wherein said target is a line image.

4. The perimeter as claimed in claim 1 wherein said target is a line image with a gap at a strategic location therein.

5. The perimeter as claimed in claim 1 wherein said transparency is divided into a plurality of image cells, each image cell containing a component of the image to be projected, and wherein the light receiving end of an optical fiber element is associated with each image cell, and said lenses being adapted to focus a coherent image onto said observation hemisphere.

6. A perimeter comprising:
   (a) an observation hemisphere having a central fixation point;

(b) means for supporting a patient's head including a chin support provided with an aperture through which the patient views the observation hemisphere and which is adjustable for proper positioning of the patient's head with respect to the central fixation point;

(c) means for projecting a target onto said observation hemisphere; and (d) fixation monitoring means for monitoring the patient's gaze during examination, said means adapted to prevent the projection of the target during periods in which the patient is not fixating on the central fixation point, said fixation monitoring means having means for directing infrared light into the patient's eye, detector means having an infrared sensor mounted on said chin support in close proximity to the patient's eye for receiving light reflected from the eye, and a focussing means for focussing the infrared light into said sensor.

7. A method of testing a patient's field of vision by perimetry comprising the steps of:

(a) positioning the patient's head with respect to the central fixation point in an observation hemisphere;

(b) obtaining fixation of the patient on the central fixation point; and (c) systematically projecting onto said observation hemisphere a target across the full assumed range of the patient's peripheral field of view; and (d) recording the patient's responses.

8. The method as claimed in claim 7 wherein said target is a line projected through 180 degrees.

9. The method as claimed in claim 7 wherein said target is a family of curves of the shape of the outline of the patient's expected field of view.

10. The method as claimed in claim 7 wherein said target is a grid of lines with arbitrary interruptions.

11. The perimeter as claimed in claim 6 wherein said fixation monitoring means also includes comparator means for comparing the output signal from said detector means during the examination with a base signal from said detector means obtained at a time of known fixation, said comparator means adapted to prevent said projection means from operating when said output and base signals differ.

12. The perimeter as claimed in claim 6 wherein said patient's head support means includes a chin support provided with an aperture through which the patient views the observation hemisphere and an upwardly extending portion covering the cheek.

* * * * *